ововв
United States Patent [19]
Skardoutos et al.

[11] Patent Number: 5,993,487
[45] Date of Patent: *Nov. 30, 1999

[54] INTEGRATED KEEL-PYLON PROSTHESIS

[75] Inventors: Wade Skardoutos, Berkley; Ken Eick, Orion, both of Mich.

[73] Assignee: Wright & Filippis, Rochester Hills, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/703,401

[22] Filed: Aug. 26, 1996

Related U.S. Application Data

[63] Continuation of application No. 08/367,031, Dec. 29, 1994, abandoned.

[51] Int. Cl.⁶ .................................. A61F 2/62; A61F 2/66
[52] U.S. Cl. .................................. 623/38; 623/27; 623/55
[58] Field of Search .................................. 623/27, 29, 33, 623/38, 47, 49, 53, 52, 55

[56] References Cited

U.S. PATENT DOCUMENTS

| | | |
|---|---|---|
| 4,473,421 | 9/1984 | Gustafsson . |
| 4,608,054 | 8/1986 | Schroder .................................. 623/27 |
| 4,696,780 | 9/1987 | Hägglund . |
| 4,938,776 | 7/1990 | Masinter . |
| 4,959,073 | 9/1990 | Merlette . |
| 5,004,477 | 4/1991 | Palfray . |
| 5,066,305 | 11/1991 | Firth . |
| 5,108,454 | 4/1992 | Rothschild et al. . |
| 5,116,381 | 5/1992 | Palfray . |
| 5,116,384 | 5/1992 | Wilson et al. .................................. 623/49 |
| 5,139,526 | 8/1992 | Skardoutos et al. . |
| 5,201,775 | 4/1993 | Arbogast et al. .................................. 623/38 |
| 5,219,364 | 6/1993 | Lloyd . |
| 5,219,365 | 6/1993 | Sabolich .................................. 623/53 |
| 5,226,918 | 7/1993 | Silagy et al. .................................. 623/33 |
| 5,336,270 | 8/1994 | Lloyd . |
| 5,376,129 | 12/1994 | Faulkner et al. .................................. 623/38 |
| 5,376,140 | 12/1994 | Ryan .................................. 623/55 |
| 5,405,410 | 4/1995 | Arbogast et al. .................................. 623/47 |
| 5,443,527 | 8/1995 | Wilson .................................. 623/49 |

FOREIGN PATENT DOCUMENTS

| | | |
|---|---|---|
| 0 648 479 A1 | 4/1995 | European Pat. Off. .................................. 623/55 |
| 0806026 | 2/1981 | U.S.S.R. . |
| 1477401 | 5/1989 | U.S.S.R. . |

OTHER PUBLICATIONS

Brochure: "Flex–Foot™ A Prosthetic Achievement In Ultra–Light Graphite Composite", FlexFoot™ Inc.
Brochure: "Walking—Steps to a Healthier Life", Flex-Foot™ Inc., ©1987.
Brochure: "Rothschilds's —Developers of the Light–Pro Series", Rothschild's Orthopedics.
Brochure: "The Seattle Foot®", Model + Instrument Development, ©, 1989.
Webster's New Riverside University Dictionary, Copyright 1984 by Houghton Mifflin Co., p. 766, 1984.

*Primary Examiner*—David H. Willse
*Attorney, Agent, or Firm*—Harness, Dickey & Pierce, P.L.C.

[57] ABSTRACT

A prosthetic component is described for use in a human lower limb prosthesis. The component can consist of an integrated pylon-keel or foot component. The preferred methods of manufacture are thermoforming or injection molding. The use of a single piece of plastic allows for improved energy storing and release characteristics while heightening the wearer's sense of weight reduction.

20 Claims, 3 Drawing Sheets

INTEGRATED KEEL-PYLON PROSTHESIS

This is a continuation of U.S. patent application Ser. No. 08/367,031 filed Dec. 29, 1994, now abandoned.

BACKGROUND OF THE INVENTION

The most common artificial leg for below knee amputees is of a rigid nature. A solid shank will connect the socket, which mounts the artificial leg to the residual limb of the amputee, and the artificial foot. The shank is often made out of a rigid alloy, such as one containing titanium or from shaped wood. The energy storing system can take the shape of a C-shaped plastic spring running from the ankle through the arch terminating towards the ball of the foot. In the case of the metal shank artificial leg, a system of this type can weigh in the range of 2½ to 4 pounds. In the case of the wood shank, the artificial leg can weigh on the order of 3 pounds.

The Flexfoot® artificial leg produced by Flexfoot, Inc., Irvine, Calif. is an example of a currently available artificial leg which exhibits a more natural dynamic action by using a flexible energy storing pylon and keel, the flexible pylon and keel being formed from a strip of laminated reinforced composite which is mechanically attached to the socket descending down to form the pylon and continuing on to form the keel of the artificial leg. Applying pressure to the Flexfoot® artificial leg (e.g. walking on it) causes flexation of the pylon and foot which acts as a spring to store energy which is also released during walking or running movement. While the Flexfoot® artificial leg allows for more natural feeling movement due to its energy storing and returning action than prior rigid artificial legs, and although the Flexfoot weighs the same as other prior artificial legs made of titanium and/or wood, its weight can be of concern to geriatric patients. The Flexfoot is also not recommended for patients with low to moderate activity levels, because of the weight and cost.

Advances in the art have also included a continuous one piece prosthesis, such as that shown in U.S. Pat. No. 5,219,360. That prosthesis offers the advantages of lightweight and improved energy storage and release characteristics. That one piece prosthesis can, however, require multiple trips to the prosthetist for fitting. In certain cases the patient may have to be fitted with another prosthesis which will be adjusted for height, pylon length, inversion, eversion, etc. Once the prosthesis is adjusted, the measurements from the adjusted prosthesis are then used to form the one piece prosthesis. This may require more than one trip to the prosthetist. Further, once the prosthesis is manufactured, adjustments may require reheating and reforming material.

SUMMARY OF THE INVENTION

This invention is directed primarily to an artificial leg or prosthesis for a below knee or above knee amputee and is fabricated out of a continuous sheet of plastic such as a polypropylene-polyethylene blend.

Specifically, the invention is directed to an integrated pylon keel prosthesis for attachment to an adjustable tube clamp, itself mounted to a socket to mount the artificial leg to the residual limb of the amputee. Alternatively, this prosthetic component can be a foot formed according to the present invention and fitted to an existing pylon or artificial leg.

The integrated keel-pylon prosthesis is formed from a single sheet of thermoformable plastic with flanges for reinforcement. In one embodiment, the hollow pylon can be reinforced and/or have its dynamic characteristics altered by reinforcement with an internal plug.

In practice, the prosthetist would perform a stump measurement on the amputee to determine the overall height of the prosthesis from which the pylon length could be determined. The prosthetist would cut a preformed integrated pylon keel prosthesis to fit the pylon to an adjustable tube clamp, whereby the clamp itself is secured to the socket. Then the prosthetist adjusts the tube clamp for inversion eversion, foot position, and rotation. An interchangeable heel wedge or foot form can be added. The stiffness of the keel and/or pylon can be adjusted by removal of material to reduce rigidity. Keel stiffness can be increased by the addition of material such as a stiffening beam to the keel. Keel and pylon stiffness can be jointly increased by insertion of an additional keel-pylon assembly.

The prosthetist may also decide to form only the foot of the prosthesis according to the invention. A preformed or custom formed foot can be trimmed to fit the pylon or leg of the prosthesis and allow through conventional means.

The foot or keel of the invention may also be padded to make a soft walker foot. The prosthetist would add one or more layers of foam to create the natural shape of the human foot. The soft walker can be used in daily activities allowing for comfortable walking.

The invention allows for decreased weight of a prosthesis. A further advantage of the invention is a decreased weight prosthesis that allows for improved energy retention and release characteristics to simulate natural feeling movement. An advantage of the invention is that it allows modification of the dynamic characteristics of the pylon, depending on the load bearing requirements of the patient. An advantage of the invention is that it allows modification to the keel dynamics, depending on the load bearing characteristics of the patient. Another advantage is increased efficiency in the manufacture of the pylon-keel element. The advantages of the use of the foot according to the invention includes the reduced weight at the end of the moment arm of the leg giving an increased perception of weight reduction.

DETAILED DESCRIPTION OF THE PREFERRED EMBODIMENT

The preferred embodiment of the invention is for lower limb prosthetics or prosthetic component.

Figure 1:
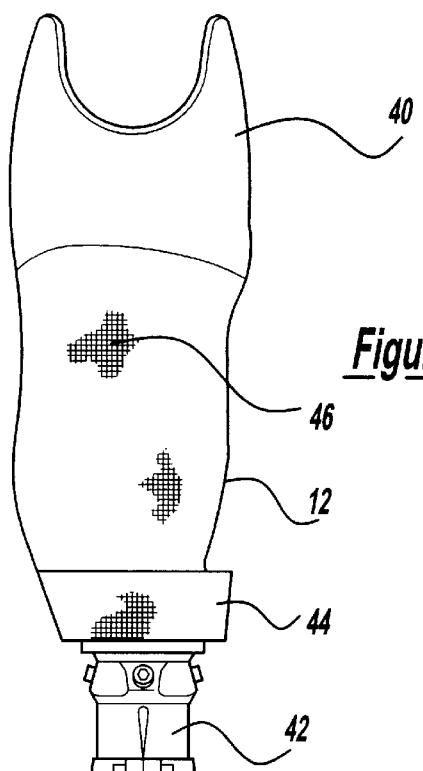
FIG. 1 is a front elevational view of the prosthesis according to the invention.

Turning to FIG. 1, a pylon-keel 10 for use in a prosthetic device 12 is illustrated. The preferred prosthetic device is designed to replicate certain functional aspects of the human leg, especially for lower limb amputees. The pylon section 14 of the pylon keel is a generally vertical component functioning to transmit forces between the residual limb of the amputee and the keel section 16. The keel section is designed to replicate the functional characteristics of the human foot, especially the force transmitting characteristics.

Figure 2:
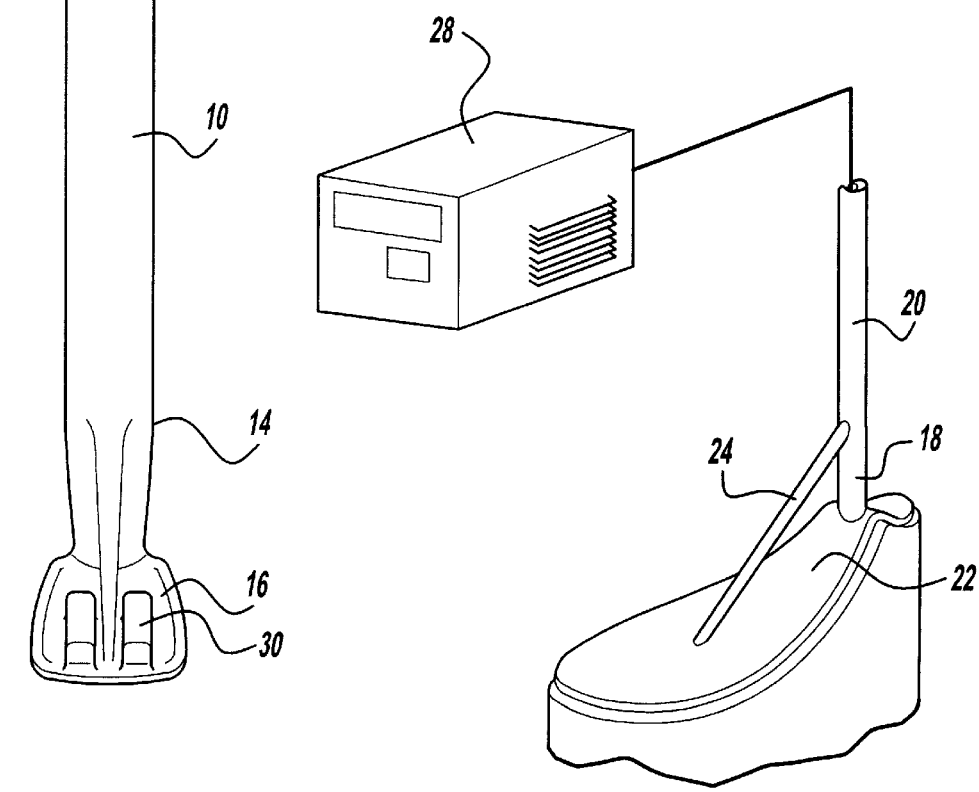
FIG. 2 is a schematic view of an assembly used to form the inventions.

Turning to FIG. 2, the method of manufacture for the pylon keel begins with a mandrel assembly 18. The mandrel assembly has a vertical tube 20 around which the pylon section will be formed, a horizontal plate or keel form 22 around which the keel section will be formed, and a wire or bar 24 which operates to establish webbing or ribbing spanning between the pylon and keel sections to rigidify and change the flex characteristics between the pylon section and keel section. The length of the vertical mandrel 20 can be adjusted to a range of sizes depending upon the type of patient to be fitted. Primarily this dimension will vary given the height of the patient and hence, the length of the amputated limb to be replaced. In addition, a variety of keel forms can be used depending upon the size of the keel section desired. Care should be taken in selecting the size of the keel form to take into consideration whether or not the final prosthesis will be an endoskeletal prosthesis and hence, need to be fitted with a conventional cover cosmetically replicating the human foot. The keel angle can also allow for heel height adjustments.

The keel form can be flat or preferably contain an arch forming hump for purpose of arch in keel.

The bar 24 allows sufficient stiffness to be cast into the keel. The exact stiffness characteristic can later be modified as explained below by removing material, or if necessary, adding material to the prosthesis. The bar 24 should be sized so that the resultant rib or web would end at the approximate location of the metatarsal heads in a natural foot. By terminating the rib at the approximate location of the metatarsal heads, the keel is more likely to flex at that location, thus approximating the flexing characteristics of the natural foot.

Once the proper mandrel assembly has been arrived at, a sheet of thermoplastic material is selected from which to fabricate the keel-pylon assembly.

The preferred material for fabricating the keel-pylon is a thermoplastic copolymer consisting of polypropylene and polyethylene. The most preferred material is a copolymer sheet consisting of 95% polypropylene and 5% polyethylene such as sold by Merimat Precision Corp., 2480 W. 82nd Street, Hialeah, Fla. 33016. The thickness of the polymer sheet is to be determined by the strength desired in the ultimate article. This in turn depends upon the weight and activity level of the patient. It has been found that ¼" thick sheet material has been suitable for moderately to highly active patients. Less active patients and/or patients of reduced weight can have successful results with a prosthesis formed from thinner material. Such patients can also benefit from further reduction of weight obtained from using thinner materials. Other mixtures of materials can also be used, as well as sheets consisting entirely of a single material such as polyethylene.

The copolymer sheet is heated in an oven to approximately 330–355° F. Care should be taken so the sheet is not overheated and loses the integrity of the copolymer mix. The sheet of heated copolymer is draped over the top of the mandrel assembly, and manually pressed to conform to the mandrel assembly. Care should be taken to have the thickness of the sheet remain uniform, that is the sheet should not be thinned in discreet areas due to stretching. Given the load bearing and force transmitting functions of the device, it is especially important not to thin the material in the segment formed over the mandrel which becomes the pylon area. The edges of the copolymer sheet are brought together along the back of the mandrel assembly and pressed together to form a flange along the posterior portion of the keel-pylon. (See FIG. 4, element 26) A vacuum is applied by the vacuum source 28 between the copolymer sheet and the mandrel assembly to more closely conform the copolymer sheet to the mandrel assembly in a vacuum forming process.

In one embodiment, the mandrel assembly is covered with a conventional nylon stocking. The nylon stocking may be further conformed to the mandrel assembly by the use of tie downs such as thread. It has been found that the nylon stocking functions to maintain air passages along the surface of the mandrel assembly. These air passages reduce the chances of bubbles forming in the final prosthesis by pockets of air trapped between the copolymer sheet and the mandrel assembly and hence allow a more definite conformance of the copolymer sheet to the mandrel assembly Further, the nylon stocking aids in removing the final assembly from the mandrel assembly. See U.S. Pat. No. 5,219,360 which is hereby incorporated by reference.

Additional reinforcement means such as a stiffening beam can be added to the keel form to stiffen the front portion of the resultant keel and create a stiffer toe lever. One method of increasing the stiffness is to mount additional polymer material onto the keel form 22 so that it is fused to the polymer sheet when it is wrapped around the assembled model.

Figure 3:
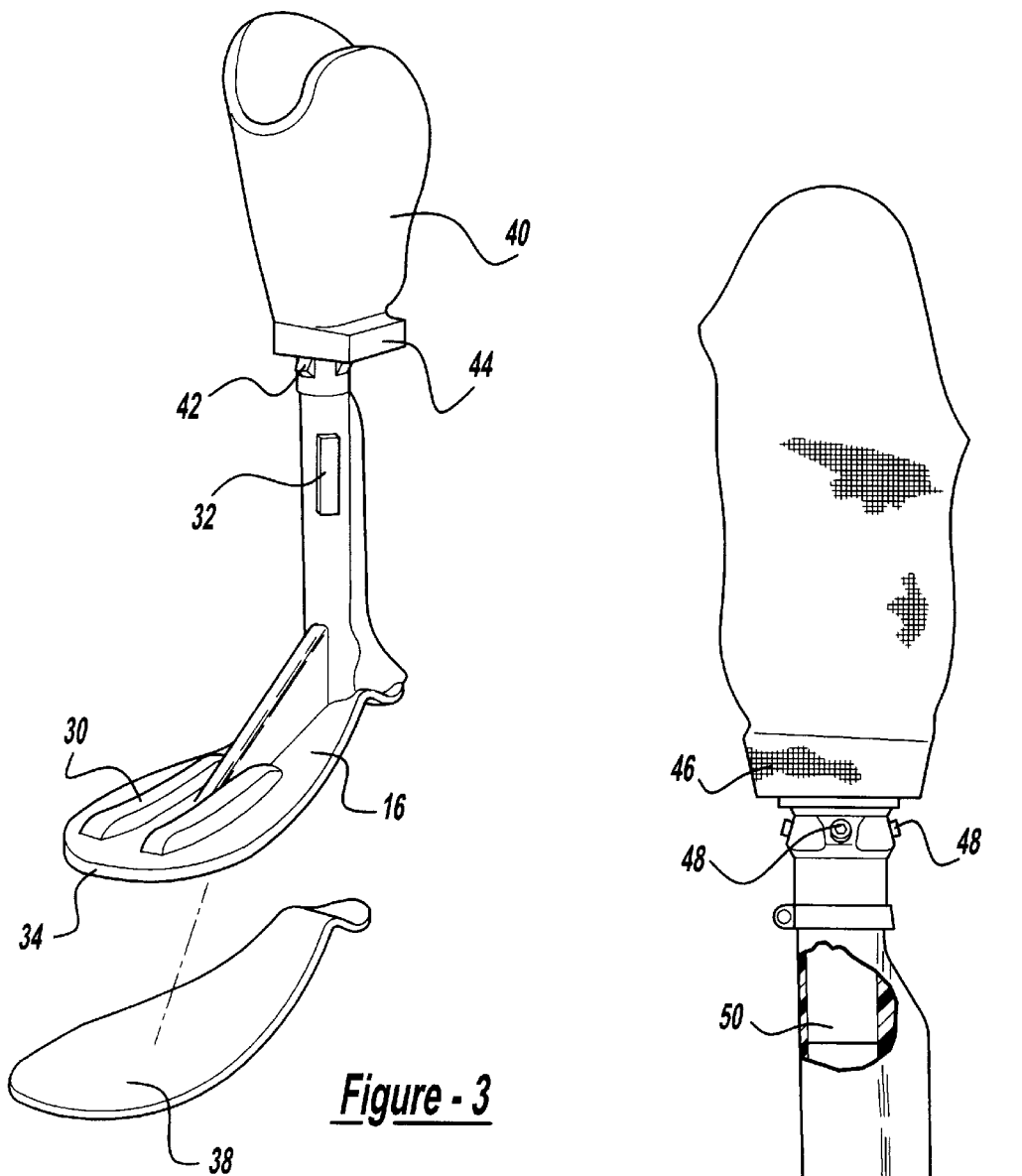
FIG. 3 is a perspective view of an assembled prosthesis according to the invention.

Turning to FIG. 3, a stiffening beam or beams 30 may be added after forming by fusing additional polymeric material on top of the formed keel 16 in order to add to a stiffer toe lever. In an effort to replicate a more natural feel, it has been found that the stiffening beam should be placed anterior to the section of the keel corresponding to the metatarsal heads. Additional reinforcing means can include springs, steel or carbon graphite composites encased in the polymer stiffening beams to form springs or stiffeners in the keel.

Additional reinforcement means can also be added to the exterior of the pylon. Segments of polymeric material can be fused to the pylon during the forming procedure. The fusing of the sheet of copolymer material upon itself to form the posterior flange along the pylon itself functions as a stiffening beam. In addition, the activities of the patient and/or placement of the keel-pylon relative to the lines of forces generated during movement of the patient may indicate placement of exterior reinforcing means 32 at different locations relative to the pylon.

Once the copolymer has cooled, the mandrel assembly is removed from the pylon keel. The resultant prosthesis component is a one piece polymeric keel-pylon. The proximal end of the pylon is trimmed to remove excessive material and burrs or sharp edges. The posterior flange is also trimmed. At this point the flange can be further modified by reduction of material to give the pylon the anterior posterior flexibility desired. This modification can also wait until the pylon keel component is fitted to the patient. The keel rim 34, the material depending downward from the border of the keel, is trimmed. The keel rim is formed from material that was formed over the sides of the horizontal plate or keel form. The keel rim should not be entirely removed, as it increases the rigidity of the keel and can serve to position and secure the sole and heel combination prosthesis or further endoskeletal prosthesis.

The interior of the keel rim may be filled by an insert 38 of Pelite® foam. This serves to block the inside of the pylon from contamination as well as to provide support for the interior of the keel rim to resist deformation of the keel, especially collapsing of the horizontal keel surface which may tend to splay out the keel rim.

Figure 4:
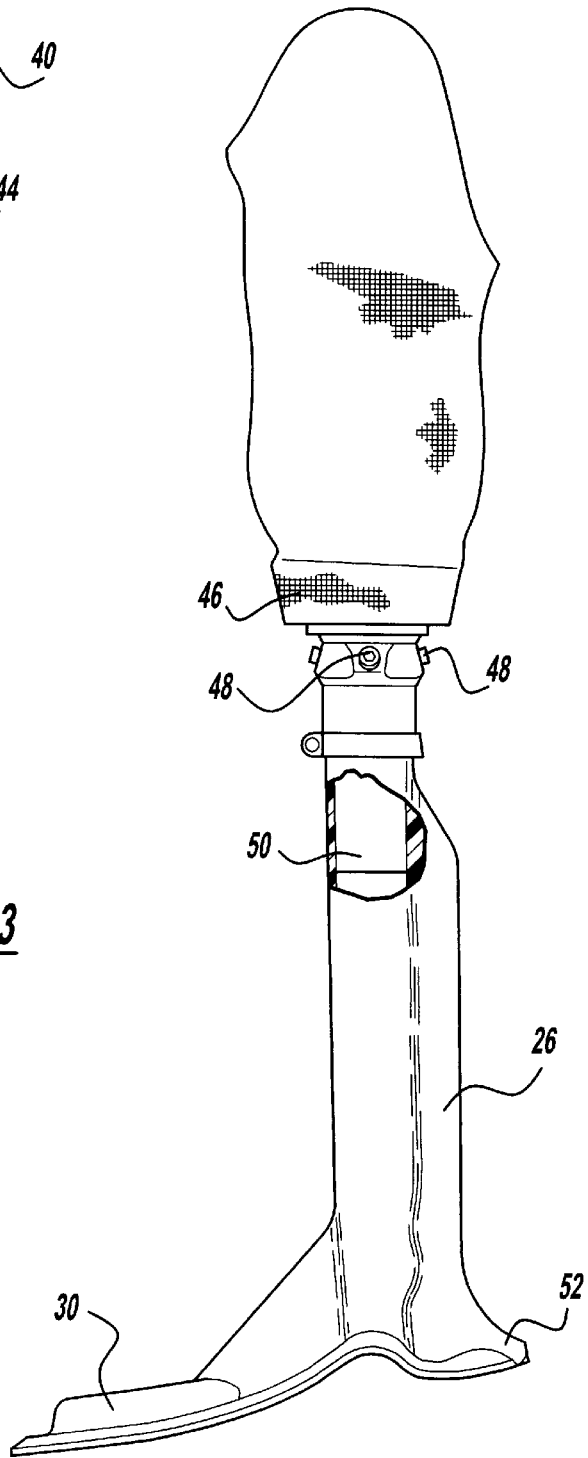
FIG. 4 is a side elevational view of a prosthesis according to the invention.

The pylon keel assembly can be fitted to the residual limb of the patient by conventional means. For example, a socket 40 is fitted to the residual limb of the patient. To the socket, is affixed an adjustable tube clamp 42 such as that made by USMC or Autobock Orthopedics Industries, Inc., 3000 Xenuim Lane, N., Minneapolis, Minn. 55441. The adjustable tube clamp is fitted to the socket by means of an attachment block 44. The attachment block is fitted to the socket by conventional means known to those in the art, including mechanical fasteners or bridging materials such as thermoset plastics, thermoformed plastics or synthetic orthopedic casting tape 46. Turning to FIG. 4, the pylon is inserted into the adjustable tube clamp and secured by the clamping action of set screws 48. The adjustable tube clamp allows for adjustment of the prosthesis in multiple planes, including adjustment for adduction, flection and extension.

In the preferred practice, the patient will have been fitted with the socket 40. The socket will possess an adjustable tube clamp. A preformed keel-pylon component is then selected. The approximate height of the keel-pylon can be determined from a prior prosthesis of the patient, or by conventional measurement techniques. As part of the fitting process, the pylon keel can be adjusted for inversion/eversion, etc. as explained above.

When mounting the keel-pylon in an adjustable tube clamp, dynamic forces are concentrated immediately around and below the collar within the pylon. Depending upon the activity level of the wearer and the material selected, a hollow pylon may collapse at that juncture. To reinforce the pylon at that area and to distribute the forces over a greater area, an insert or plug 50 may be used. The insert can be combined with the pylon keel during the molding operation described above, or may be inserted subsequently. The preferred material for the insert is a fiberglass rod. Alternative materials include Kevlar, Delron, carbon graphite and/or nylon. The insert spreads the forces over a greater length of pylon so as to reduce the possibility of pylon collapse. The preferred length of the insert is approximately 4" and should extend from the very top of the pylon in a downward direction. The insert may be further used to modify flexibility of the pylon such as to provide a more rigid feel for the wearer.

During fitting, a foot shell may be added in addition to or in substitute for a heel sole prosthesis. An example of such a foot shell would be the Carbon Copy III foot shell from Ohio Willowood Company. The foot shell generally would envelope the keel portion of the pylon keel. Depending on the intended use of the pylon keel. A tab 52 may be formed as part of the flange so as to assist in retaining the foot shell to the prosthesis.

If further adjustment of the dynamic action of the pylon keel is desired, such as for athletic patients who wish to modify the characteristics for participation in sports, a secondary pylon and/or pylon and keel assembly can be added. The supplemental pylon or pylon keel assembly is sized to fit within the interior of the pylon of the prosthesis with any heel portion fitting within the keel portion of the prosthesis. In use, this would involve removing the sole prosthesis 38 and/or foot shell and insertion of the supplemental pylon. The supplemental pylon and/or pylon keel assembly is useful for providing more energy storage in for example, the toe section. The additional pylon can also reduce flexing during strenuous activities. Additionally, the supplemental pylon and/or pylon keel assembly can be formed for a different flex of the foot such as that corresponding to the natural toe being plantar flexed. The use of the supplemental pylon keel assembly will alter the energy returning sensation from that given by the basic pylon keel assembly.

Figure 5:
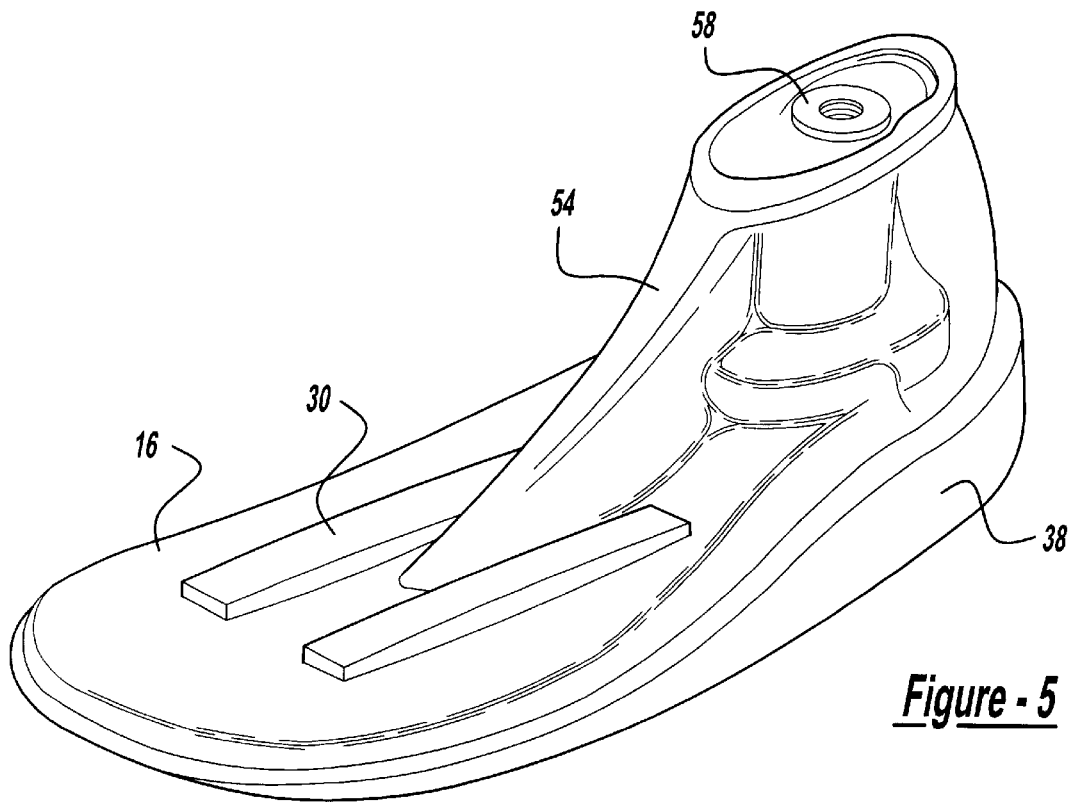
FIG. 5 is a perspective view of a foot prosthetic component according to the invention.
Figure 6:
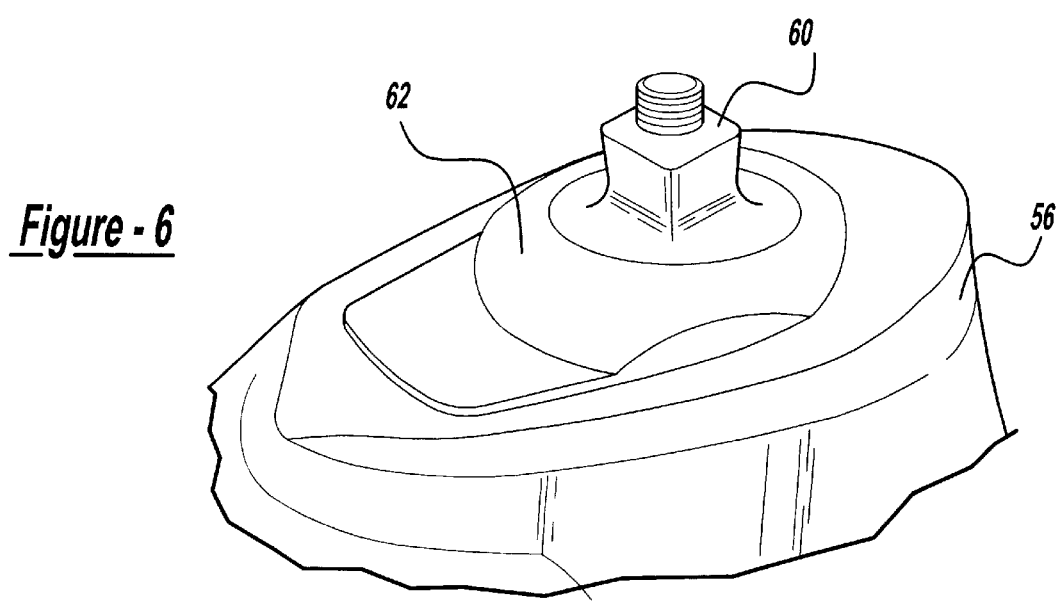
FIG. 6 is a perspective view of a portion of a foot prosthesis component according to the invention.

FIGS. 5 and 6 illustrate forms of the invention for use as the foot component 54, 56 of a prosthesis (not shown in FIG. 5 and 6). The foot component is formed as described above to create the keel 16. In addition, the area corresponding to the ankle has attachment means 58, 60 molded therein. The attachment means are conventionally used with threaded fasteners for mounting the foot to a pylon or artificial leg. The attachment means can include adjustment means for orientating the foot to the leg in the proper anatomical planes as is known in the art by using a titanium ankle adapter 62. The attachment of the foot to the pylon or leg is preferably a rigid attachment. The lightweight foot component 54, 56 can result in greater patient comfort and mobility because the weight saving is at the end of the moment arm defined by the leg or the leg below the knee. Thus, the perception of weight savings to the bearer is increased as less mass is swung through the longest chord of the arc described when walking or running. For example, a soft walker may be fifty percent lighter than conventional system, but be perceived to be on the order of 70–80% lighter by the wearer.

The invention may also be used for above knee amputees. The pylon 14 is longer to allow the component to be mated to an existing prosthesis at approximately the level of the original knee.

The invention may also be formed by injection molding. The invention allows for standard sizes to be produced from a mold. The resultant molded articles can be trimmed or modified as explained above to fit the particular wearer. The ability to standardize sizes can make the mold investment worthwhile. The prosthetist can still make custom sizes or features according to the vacuum forming technique discussed above.

While the above detailed description describes the preferred embodiments of the present invention, it will be understood that the present invention is susceptible to modification, variation and alteration without deviating from the scope of the fair meaning of the subjoined claims.

What is claimed is:

1. A human leg prosthesis comprising:
   a socket for adapting said prosthesis to a residual limb;
   a tube clamp secured to said socket; and
   a thermoformed plastic pylon-keel, said thermoformed plastic pylon-keel being monolithic and formed from a single sheet of thermoplastic material to include a keel with a toe and a heel and an elongated tube portion said elongated tube portion including a terminal end and said tube clamp circumferentially engaging substantially the entire periphery of said terminal end of said pylon-keel for adjustably securing said terminal end to said tube clamp, said pylon-keel being adjustable in said tube clamp in at least two planes.

2. The prosthesis of claim 1 wherein said pylon-keel is thermoformed from a single piece of material comprising polypropylene.

3. The prosthesis of claim 1 wherein said pylon-keel is thermoformed from a single piece of material comprising polyethylene.

4. The prosthesis of claim 1 wherein said pylon-keel is thermoformed from a single piece of material comprising a mix of polypropylene and polyethylene.

5. The prosthesis of claim 1 further comprising a reinforcing insert disposed within said pylon-keel.

6. The prosthesis of claim 5 wherein said reinforcing insert is disposed within said pylon-keel in a region of said tube clamp.

7. The prosthesis of claim 1 wherein said pylon-keel further comprises a flange along a posterior edge of said pylon-keel.

8. The prosthesis of claim 1 further comprising an anterior rib bridging the pylon-keel.

9. The prosthesis of claim 8 further comprising a reinforcing beam fused to said pylon-keel to resist bending of said pylon-keel.

10. The prosthesis of claim 9 further comprising a foot shell.

11. A monolithic plastic pylon-keel manufactured from a single sheet of thermoformable plastic material, said plastic pylon-keel including a keel with a toe and heel and an elongated tube portion with a terminal end portion, said tube portion having a substantially constant circumference through said terminal end portion, said circumference of said terminal end portion configured to be received by a tube clamp, and said pylon-keel being adjustable in at least two planes in said tube clamp for use in a human leg prosthesis.

12. A human leg prosthesis for a below knee amputee comprising:

a monolithic pylon-keel manufactured from a single sheet of thermoplastic material for at least two plane adjustable attachment to a socket means, said pylon-keel including a keel with a toe and heel and an elongated tube portion with a terminal end portion on said elongated tube portion, said tube portion having a substantially constant circumference through said terminal end portion, a socket means coupled with said circumference of said terminal end portion; and an anterior stiffening rib integrated between a pylon and keel of said pylon-keel.

13. The prosthesis of claim 12 further comprising a keel stiffening beam fused to said pylon-keel behind the metatarsal head region.

14. The prosthesis of claim 12 further comprising a load distributing insert disposed within said pylon-keel adjacent a proximal end.

15. The prosthesis of claim 12 weighing less than about 20 ounces.

16. A prosthetic component for a human lower limb prosthesis comprising:

a monolithic plastic foot component formed from a single sheet of thermoplastic material having a keel section with an ankle section, heel section, toe section, and an anterior rib;

an attachment means molded into said foot component for threadingly engaging a pylon component; and said anterior rib extending between said attachment means and said toe section and formed with said keel.

17. The prosthetic component of claim 16 wherein said foot component is thermoformed from a single piece of plastic.

18. The prosthetic component of claim 16 wherein said foot component is injection molded.

19. A lower limb prosthetic component for use in replacing a human leg comprising:

a plastic pylon adapted to engage a knee prosthesis, said pylon being an elongated plastic tube and including a terminal end portion having a circumference for securing said pylon with a clamp, said tube having a substantially constant circumference through said terminal end portion;

a clamp secured with the knee prosthesis and said pylon being adjustable in said clamp in at least two planes; and a keel monolithic with said pylon while allowing flexing of said keel at the area corresponding to the metatarsal heads, said keel also including a heel portion and a toe portion.

20. The component of claim 19 wherein said keel and pylon are formed from the same single sheet of polyethylene containing material.

* * * * *